US007598408B2

(12) United States Patent
Imahori et al.

(10) Patent No.: US 7,598,408 B2
(45) Date of Patent: Oct. 6, 2009

(54) INTERMEDIATES FOR SYNTHESIS OF VITAMIN D DERIVATIVES

(75) Inventors: Hidekazu Imahori, Kobe (JP); Hiroya Koyama, Kobe (JP); Daisuke Yoshihara, Kobe (JP); Yoshinori Sawashita, Kobe (JP); Sota Kurita, Kobe (JP); Yoshihiro Ichihara, Kobe (JP); Yoshihiro Takagi, Kobe (JP); Katsutoshi Hirose, Kobe (JP)

(73) Assignee: KNC Laboratories Co., Ltd., Hyogo (JP)

( * ) Notice: Subject to any disclaimer, the term of this patent is extended or adjusted under 35 U.S.C. 154(b) by 410 days.

(21) Appl. No.: 10/546,150

(22) PCT Filed: Feb. 18, 2004

(86) PCT No.: PCT/JP2004/001831

§ 371 (c)(1),
(2), (4) Date: Aug. 22, 2005

(87) PCT Pub. No.: WO2004/076468

PCT Pub. Date: Sep. 10, 2004

(65) Prior Publication Data

US 2006/0106242 A1   May 18, 2006

(30) Foreign Application Priority Data

Feb. 25, 2003   (JP)   ............... 2003-046992

(51) Int. Cl.
*C07F 7/18*   (2006.01)
*C07F 7/08*   (2006.01)

(52) U.S. Cl. ............................... 556/9; 556/12

(58) Field of Classification Search ....................... None
See application file for complete search history.

(56) References Cited

U.S. PATENT DOCUMENTS

| 5,086,191 A | 2/1992 | De Luca et al. |
| 5,536,713 A | 7/1996 | De Luca et al. |
| 5,886,233 A | 3/1999 | Steinmeyer et al. |

FOREIGN PATENT DOCUMENTS

| JP | 20250844 A | 10/1990 |
| JP | 5-186421 | 7/1993 |
| JP | 10-502061 A | 2/1998 |
| JP | 2001-504135 | 3/2001 |
| WO | 98/41501 | 9/1998 |
| WO | 00/10548 | 3/2000 |
| WO | 01/03704 A1 | 1/2001 |
| WO | WO0118003 | * 3/2001 |
| WO | 01/72292 A2 | 10/2001 |
| WO | 01/74765 A1 | 10/2001 |
| WO | 01/74766 A1 | 10/2001 |
| WO | 01/92221 A1 | 12/2001 |
| WO | 02/05823 A2 | 1/2002 |
| WO | 02/05824 A1 | 1/2002 |
| WO | 02/20021 A1 | 3/2002 |

OTHER PUBLICATIONS

Kirsch et al (Synthesis 2003, No. 12, 1827-1836).*
Hilpert et al (Tetrahedron 57 (2001) 681-694).*
Wang et al (J. Org. Chem. 1998, 63, 3051-3058).*
Parker et al (Journal of Organic Chemistry (1997), 62(19), 6692-6696).*
Rücker, G. et al., "Stereoselective Reduction of Cyclic 2,3-Epoxyketones to Trans-2,3-Epoxyalcohols", *Synthetic Communications*, vol. 10, No. 8, pp. 623 to 626 (1980).
Barbier, P. et al., "Efficient Fluorination with Tetrabutylammonium Dihydrogen Trifluoride in a Novel Approach toward 1-α-Fluoro-25-hydroxy-vitamin $D_3$ Analogues", *Journal of Organic Chemistry*, vol. 63, No. 20, pp. 6984 to 6989 (1998).
Wang, J. et al., "Enantioselective Approach to the Synthesis of Cyclohexane Carbocyclic Nucleosides", *Journal of Organic Chemistry*, vol. 163, No. 9, pp. 3051 to 3058 (1998).
Hatakeyama, S. et al., "Efficient enantio specific synthesis of key-A-ring synthons for the preparation of 1α, 25-dihydroxyvitamin D3 using a chromium(II)-mediated reaction", *Journal of Organic Chemistry*, vol. 54, No. 15, pp. 3515 to 3517 (1989).
Knoelker, H. et al., Enantioselective synthesis of calcitriol A-ring fragments, *Tetrahedron*, vol. 53, No. 1, pp. 91 to 108 (1997).

* cited by examiner

*Primary Examiner*—Brian J Davis
(74) *Attorney, Agent, or Firm*—Wenderoth, Lind & Ponack, L.L.P.

(57) ABSTRACT

The present invention provides a novel intermediate for synthesizing vitamin D derivatives by using a less expensive material. That is, the present invention provides a compound which is synthesized by using carvone as a starting material and which is represented by the following formulae.

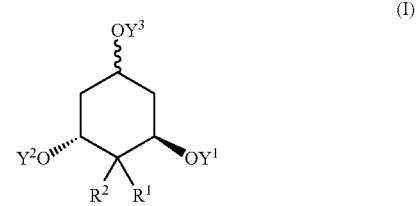

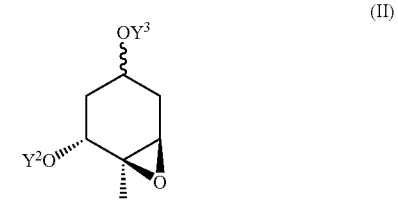

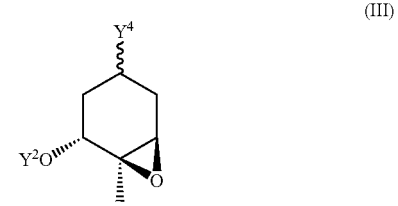

6 Claims, 1 Drawing Sheet

INTERMEDIATES FOR SYNTHESIS OF VITAMIN D DERIVATIVES

TECHNICAL FIELD

The present invention relates to novel synthetic intermediates for the total synthesis of vitamin D derivatives and, more particularly, it relates to intermediates for 19-nor-vitamin D derivatives where exo-methylene group constituting a double bond outside the A ring of vitamin D derivatives is substituted with two hydrogen atoms.

BACKGROUND ART

With regard to natural vitamins showing a high biologically effective value, there are $D_2$ (ergocalciferol) and $D_3$ (cholecalciferol) and physiological actions of those vitamin D derivatives in human body are same. Those vitamin D derivatives are synthesized in human skin by action of ultraviolet ray and their structures change in kidney and liver to give active-form vitamin D derivatives whereby a physiological action is firstly achieved. The active-form vitamin D is a kind of hormone and its action mechanism is similar to a steroid hormone. Thus, it is bonded to a receptor existing in cell nucleus and controls the transcription of specific genes whereupon the activity is finally achieved.

With regard to 1α,25-dihydroxyvitamin $D_3$ which is an active-form vitamin D, many structural analogs have been prepared and their activities have been tested already. Some of those compounds show a significant effect concerning cell differentiation and calcium adjustment and, therefore, they have been known to be useful for the treatment of various diseases such as renal osteodystrophy, vitamin D-resistant rickets, osteoporosis, psoriasis and cancer.

A novel group of vitamin D analogs where an exo-methylene group (C-19) specific to vitamin D derivatives is substituted with two hydrogen atoms or 19-nor-vitamin D derivatives such as 1α,25-dihydroxy-19-nor-vitamin $D_3$ have been prepared and their biological test has been conducted already. It has been clarified that those compounds show a selective activity profile and a very low calcium transfer activity having a high efficacy for induction of cell differentiation. Therefore, those compounds have been proposed as treating agents not only for malignant tumor, leukemia, cancer, cancer of the colon, breast cancer and prostatic cancer but also for osteomalacia, senile osteoporosis, postmenopausal osteoporosis, steroid-induced osteoporosis, osteoporosis due to low turnover of bone, renal osteodystrophy, psoriasis, imbalance of immune system, multiple sclerosis, diabetes mellitus, refusal for transplantation or various skin disorders (Japanese Patent Laid-Open No. 05/186,421, U.S. Pat. No. 5,086,191, WO 01/92221, WO 02/05823, WO 01/74765, WO 02/20021, WO 01/74766, WO 02/05824, WO 00/10548, WO 01/03704, WO 01/72292, etc.).

The desired 19-nor-vitamin D derivatives are prepared by the reaction of Windaus Grudman ketone with phosphine oxide in the presence of a base followed, if necessary, by removing the protective group. Here, phosphine oxide is synthesized via many steps using quinic acid as a starting material (the reaction step formula 1 in Japanese Patent Laid-Open No. 05/186,421).

Recently, compounds in which 2-position of 1α,25-dihydroxy-19-nor-vitamin $D_3$ is substituted with hydroxyl group or an alkoxy group has been synthesized as well (U.S. Pat. No. 5,536,713).

In addition, 2-alkylidene-19-nor-vitamin D compounds, particularly 2-methylene-19-nor-vitamin D compounds, having an alkylidene group (particularly, methylene group) at 2-position where an exoalkylidene group of A ring of 1α,25-dihydroxy-vitamin $D_3$ is transferred from carbon 10 (C-10) to carbon 2 (C-2) has been receiving public attention since the relatively small alkylidene (particularly, methylene) group at C-2 does not inhibit a vitamin D receptor (Japanese Patent Laid-Open No. 2001/504,135). This compound is also able to be synthesized by the reaction of Windaus Grudman ketone with phosphine oxide having a methylene group at C-2 in the presence of a base followed, if necessary, by removing the protective group. Here, the phosphine oxide having a methylene group at C-2 is also able to be synthesized via many steps using quinic acid as a starting material (scheme I of Japanese Patent Laid-Open No. 2001/504,135).

However, in the above-mentioned method, quinic acid which is expensive is used and, therefore, cost of the synthesized vitamin D derivative also becomes high. Therefore, there has been a demand for the synthesis of vitamin D derivatives from less expensive materials.

SUMMARY OF THE INVENTION

The present inventors have carried out intensive investigations for solving such problems and found to produce phosphine oxide using carvone such as (R)-(−)-carvone instead of quinic acid as a starting material whereupon the present invention has been achieved. According to the present invention, it is now possible to synthesize the desired vitamin D derivatives from carvone which is a less expensive material.

Thus, the present invention relates to a compound represented by the following formula (I).

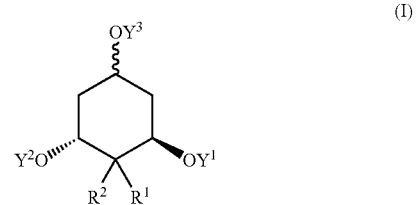

(In the formula, $Y^1$ and $Y^2$ may be same or different and each is hydrogen atom or a protective group for hydroxyl group; $Y^3$ is hydrogen atom or a protective group for hydroxyl group where a group $Y^3O$— may be either in R configuration or S configuration; $R^1$ and $R^2$ may be same or different and each is a group selected from the group consisting of hydrogen atom, heavy hydrogen atom, fluorine atom, hydroxyl group, protected hydroxyl group, alkyl group, aryl group, alkoxy group, hydroxyalkoxy group, fluoroalkoxy group, arylalkoxy group, aryloxy group, amino group and —$NR^3R^4$ (in which $R^3$ and $R^4$ may be same or different and each is selected from the group consisting of hydrogen atom, alkyl group, aryl group, hydroxyalkyl group, fluoroalkyl group and acyl group) or $R^1$ and $R^2$ may be bonded together to give an alkene structure =$CB^1B^2$ or an imine structure =$NB^3$; $B^1$ and $B^2$ may be same or different and their steric configuration may be either E configuration or Z configuration; $B^1$, $B^2$ and $B^3$ each is a group selected from the group consisting of hydrogen atom, heavy hydrogen atom, fluorine atom, hydroxyl group, protected hydroxyl group, alkyl group, aryl group, alkoxy group, hydroxyalkoxy group, fluoroalkoxy group, arylalkoxy group and aryloxy group or $B^1$ and $B^2$ may be bonded together to give a —$(CH_2)_x$— group (in the formula, x is an integer of 2 to 5); and $R^1$ and $R^2$ each may be in either R configuration or S configuration.)

The present invention also relates to a compound represented by the following formula (II) used as an intermediate for the synthesis of the compound represented by the above formula (I).

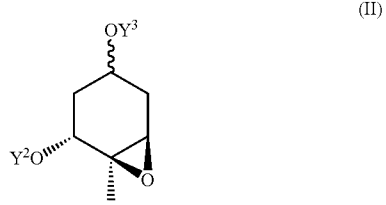

(In the formula, $Y^2$ and $Y^3$ may be same or different and each is hydrogen atom or a protective group for hydroxyl group; and a $Y^3O$— group may be in either an R configuration or S configuration.)

DETAILED DESCRIPTION OF THE INVENTION

Figure 1:
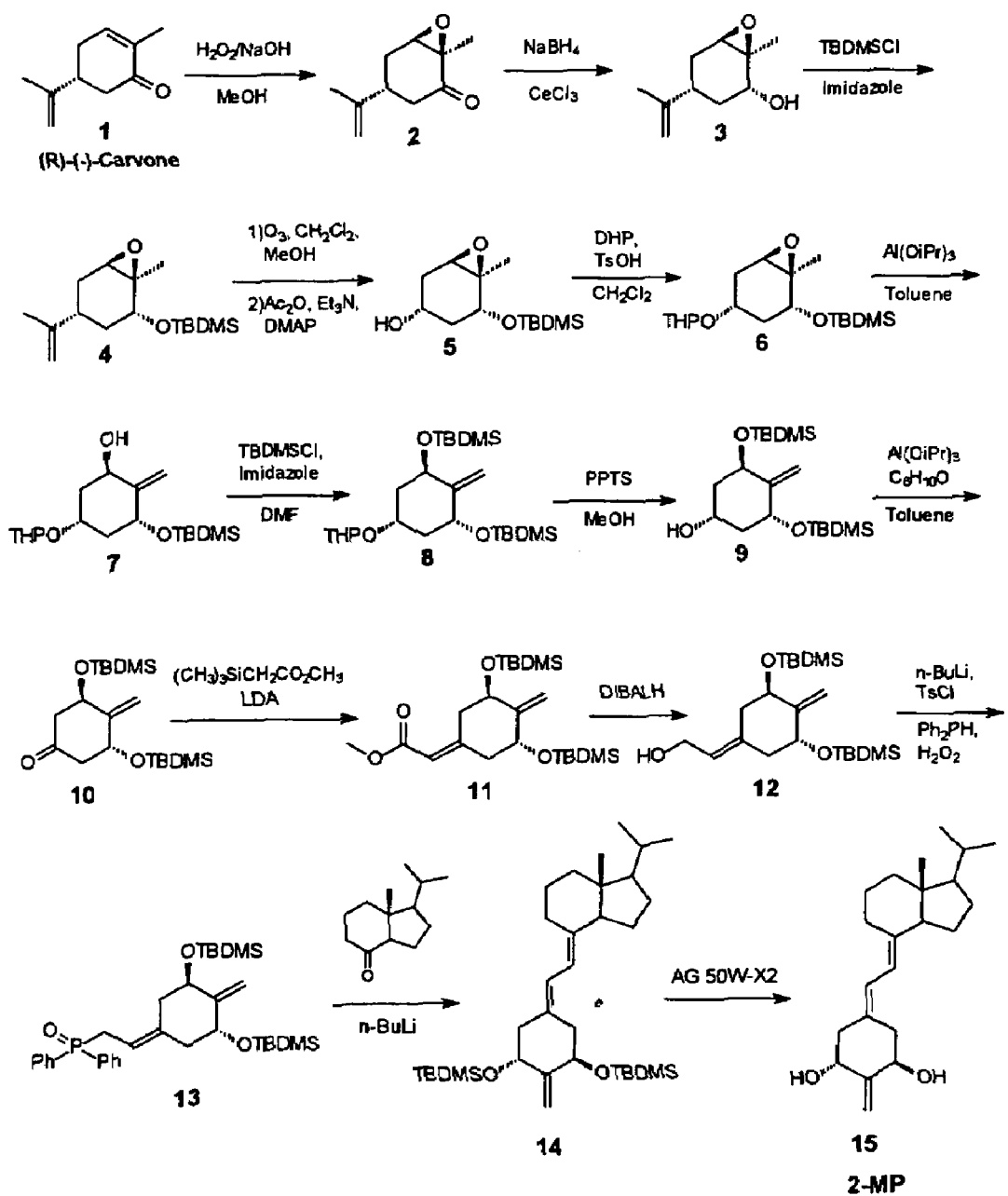
FIG. 1 is an outline of the scheme for the synthesis of a 2-methylene-19-nor-vitamin D derivative (2-MP) from carvone via the compound of the present invention.

Examples of the carvone which is a starting material for the compounds of the present invention are (R)-(−)-carvone and (S)-(+)-carvone. A step for the production of (1S-(1α,2α,4α,6α))-1-methyl-4-(1-methylethenyl)-7-oxabicyclo-[4.1.0]heptan-2-ol (compound 3) which is a precursor of the compounds of the present invention from those carvones is known already (cf. FIG. 1). The step is mentioned, for example, in *Synthetic Communication*, 10(8), 1980, 623 and *Journal of Organic Chemistry*, 63(20), 1988, 6984.

In the compound represented by the formula (I), examples of a protective group for hydroxyl group are a silyl group such as tert-butyldimethylsilyl, trimethylsilyl, triphenylsilyl, triethylsilyl and tert-butyldiphenylsilyl; a substituted alkyl group such as methoxymethyl, ethoxymethyl and methoxyethoxymethyl; an aralkyl group such as benzyl and p-methoxyphenylmethyl; an acyl group such as acetyl group and benzoyl group; an alkyl group such as methyl group, ethyl group, propyl group, isopropyl group and butyl group; tetrahydro-2-pyranyl group; and tetrahydrofuranyl group.

With regard to the compound represented by the formula (I), specific examples are the following compounds.

Firstly, there are compound where $Y^1$ and $Y^2$ are protective group for hydroxyl group, $Y^3$ is hydrogen atom, $Y^3O$— group is in an R configuration or an S configuration and $R^1$ and $R^2$ are bonded together to form a methylene group in the formula (I). To be more specific, there are a compound where $Y^1$ and $Y^2$ are tert-butyldimethylsilyl group, $Y^3$ is hydrogen atom and $R^1$ and $R^2$ are bonded together to form methylene group or (3R,5R)-3,5-bis[(tert-butyldimethylsilyl)oxy]-4-methylenecyclohexanol (compound 9), a compound where $Y^1$ and $Y^2$ are tert-butyldimethylsilyl group, $Y^3$ is hydrogen atom and $R^1$ and $R^2$ each is hydrogen atom or (3R,5R)-3,5-bis[(tert-butyldimethylsilyl)oxy]-cyclohexanol, and the like.

There are also compounds where $Y^1$ and $Y^2$ are protective group for hydroxyl group, $Y^3$ is also a protective group for hydroxyl group where $Y^3O$— is in an R configuration or an S configuration and $R^1$ and $R^2$ are bonded together to form methylene group. To be more specific, there are a compound where $Y^1$ and $Y^2$ are tert-butyldimethylsilyl group, $Y^3$ is tetrahydro-2-pyranyl group and $R^1$ and $R^2$ are bonded together to form methylene group or (3R,5R)-3,5-bis[(tert-butyldimethylsilyl)oxy]-4-methylene-1-(tetrahydro-2-pyranyloxy) cyclohexane (compound 8) and a compound where $Y^1$ and $Y^2$ are ter-butyldimethylsilyl group, $Y^3$ is tetrahydro-2-pyranyl group and $R^1$ and $R^2$ each is hydrogen atom or (3R,5R)-3,5-bis[(tert-butyldimethylsilyl)oxy]-1-(tetrahydro-2-pyranyloxy)cyclohexane.

There are also compounds where $Y^1$ is hydrogen atom, $Y^2$ and $Y^3$ are protective group for hydroxyl group where $Y^3O$— group is in an R configuration or an S configuration and $R^1$ and $R^2$ are bonded together to form methylene group. To be more specific, there are a compound where $Y^1$ is hydrogen atom, $Y^2$ is tert-butyldimethylsilyl group, $Y^3$ is tetrahydro-2-pyranyl group where $Y^3O$— is in an R configuration and $R^1$ and $R^2$ are bonded together to form methylene group or (1R-(1β,3α,5α))-3-[(tert-butyldimethylsilyl)oxy]-2-methylene-5-(tetrahydro-2-pyranyloxy)cyclohexanol (compound 7) and a compound where $Y^3$ is tetrahydro-2-pyranyl group where $Y^3O$— is in an R configuration and $R^1$ and $R^2$ are hydrogen atom or (1R-(1β,3α,5α))-3-[(tert-butyldimethylsilyl) oxy]-5-(tetrahydro-2-pyranyloxy)cyclohexanol.

In the compound represented by the formula (II) used as an intermediate for the synthesis of the compound represented by the formula (I), a protective group for hydroxyl group is the same as the protective group for hydroxyl group in the compound represented by the above formula (I). With regard to such a compound, there are (1) a compound where $Y^2$ and $Y^3$ are protective group for hydroxyl group where $Y^3O$— is in an R configuration or an S configuration or, to be more specific, a compound where $Y^2$ is tert-butyldimethylsilyl group and $Y^3$ is tetrahydro-2-pyranyl group where $Y^3O$— group is in an R configuration or (1R-(1α,2α,4α,6α))-2-[(tert-butyldimethylsilyl)oxy]-1-methyl-4-(tetrahydro-2-pyranyloxy)-7-oxabicyclo[4.1.0]heptane (compound 6), (2) a compound where $Y^2$ is a protective group for hydroxyl group, $Y^3$ is hydrogen atom where $Y^3O$— is in an R configuration or, to be more specific, a compound where $Y^2$ is tert-butyldimethylsilyl group and $Y^3$ is hydrogen atom where $Y^3O$— group is in an R configuration or (1R-(1α,2α,4α,6α))-2-[(tert-butyldimethylsilyl)oxy]-1-methyl-7-oxabicyclo[4.1.0]heptan-4-ol (compound 5), and (3) a compound where $Y^2$ and $Y^3$ are hydrogen atom and the like.

In the compound represented by the formula (III) used as an intermediate for the synthesis of the above-mentioned compound represented by the formula (I), a protective group for hydroxyl group is the same as a protective group for hydroxyl group in the above-mentioned compound represented by the formula (I). With regard to such a compound, there are a compound where $Y^2$ is a protective group for hydroxyl group, $Y^4$ is 1-methylethenyl group and $Y^4$ is in an R configuration or an S configuration or, to be more specific, a compound where $Y^2$ is tert-butyldimethylsilyl group and $Y^4$ is in an R configuration or (1R-(1α,2α,4α,6α))-2-[(tert-butyldimethylsilyl)oxy]-1-methyl-4-(1-methylethenyl)-7-oxabicyclo[4.1.0]heptane (compound 4) and the like.

An outline scheme of an example for the synthesis of a vitamin D derivative (2-MP) form carvone such as (R)-(−)-carvone via a synthetic intermediate of the present invention is shown in FIG. 1. In the drawing, each number (integer) is an abbreviation for each of the compounds. Other abbreviations show the following compounds or groups. Thus, TBDMSCl is tert-butyldimethylchlorosilane; TBDMSO is tert-butyldimethylsilyloxy group; DMAP is N,N'-dimethyl-4-aminopyridine; DHP is 3,4-dihydro-2H-pyran; TsOH is tosylsulfonic acid; THPO is tetrahydro-2-pyranyloxy group; PPTS is pyridinium p-toluenesulfonate; LDA is lithium diisopropylamide; DIBALH is diisobutylaluminum hydride; AG50W-X2 is an ion-exchange resin manufactured by Bio-Rad Laboratories Inc.; and 2-MP is 1α-hydroxy-2-methylene-19-nor-17-isopropyl-calciferol. FIG. 1 shows an example for the production of vitamin D derivatives and the present invention is not limited to the synthetic route shown by FIG. 1.

A process for the production of (1S-(1α,2α,4α,6α))-1-methyl-4-(1-methylethenyl)-7-oxabicyclo-[4.1.0]heptan-2-ol (compound 3) from (R)— (−)-carvone (compound 1) is known already and is mentioned, for example, in *Synthetic Communication,* 10(8), 1980, 623 and *Journal of Organic Chemistry,* 63(20), 1988, 6984. FIG. 1 shows an example of a process for the production of (1S-(1α,2α,4α,6α))-1-methyl-4-(1-methylethenyl)-7-oxabicyclo-[4.1.0]heptan-2-ol (compound 3) from (R)-(−)-carvone (compound 1) via (1R-(1α,4α,6α)-1-methyl-4-(1-methylethenyl)-7-oxabicyclo[4.1.0]heptan-2-one (compound 2).

In FIG. 1, (R)-(−)-carvone (compound 1) is dissolved in a solvent such as methanol, hydrogen peroxide is added thereto, a reaction is carried out by further addition of sodium hydroxide under cooling with ice and an epoxy ring is formed from a double bond of a cyclohexene ring to produce (1R-(1α,4α,6α))-1-methyl-4-(1-methylethenyl)-7-oxabicyclo-[4.1.0]heptan-2-one (compound 2).

After that, the above-mentioned compound 2 is dissolved in a polar solvent such as methanol, a catalyst such as cerium chloride (III) heptahydrate is added thereto and a reaction is carried out by addition of a reducing agent such as sodium borohydride under cooling with ice so that carbonyl group at 2-position is converted to hydroxyl group to produce (1S-(1α,2α,4α,6α))-1-methyl-4-(1-methylethenyl)-7-oxabicyclo-[4.1.0]heptan-2-ol (compound 3).

The above-mentioned compound 3 is further dissolved in a solvent such as DMF, a base such as imidazole is added thereto and a reaction is carried out by addition of tert-butyldimethylsilylating agent such as tert-butyldimethylchlorosilane under cooling with ice so that hydroxyl group at 2-position is protected as tert-butyldimethylsilyloxy group to produce (1R-(1α,2α,4α,6α))-2-[(tert-butyldimethylsilyl)oxy]-1-methyl-4-(1-methylethenyl)-7-oxabicyclo[4.1.0]heptane (compound 4). Said compound is a kind of the compound represented by the formula (III). Its chemical formula is shown below.

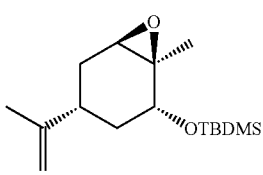

4

After that, the above-mentioned compound 4 is dissolved in a solvent such as methanol and methylene chloride, then ozone gas, for example, is introduced thereinto at −65° C. followed by substituting with nitrogen gas and a reaction is carried out by addition of acetic anhydride in the presence of a base such as triethylamine and a catalyst such as N,N′-dimethyl-4-aminopyridine so that 1-methylethenyl group at 4-position is substituted with hydroxyl group via acetoxy group to produce (1R-(1α,2α,4α,6α))-2-[(tert-butyldimethylsilyl)oxy]-1-methyl-7-oxabicyclo[4.1.0]heptan-4-ol (compound 5). Said compound is a kind of the compound represented by the formula (II). Its chemical formula is as shown below.

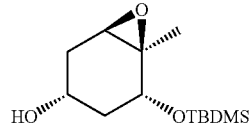

5

Then the above-mentioned compound 5 is dissolved in a solvent such as methylene chloride and a reaction is carried out by addition of an acid catalyst such as p-toluenesulfonic acid and 3,4-dihydro-2H-pyran (DHP) so that hydroxyl group at 4-position is protected as tetrahydro-2-pyranyloxy group to produce (1R-(1α,2α,4α,6α))-2-[(tert-butyldimethylsilyl)oxy]-1-methyl-4-(tetrahydro-2-pyranyloxy)-7-oxabicyclo [4.1.0]heptane (compound 6). Here, it is also possible to use other compound which forms a protective group for hydroxyl group such as acetyl chloride, methoxymethyl chloride or benzoyl chloride instead of 3,4-dihydro-2H-pyran (DHP) to protect the hydroxyl group at 4-position. The resulting compound is a kind of the compound represented by the formula (II). Its chemical formula is shown below.

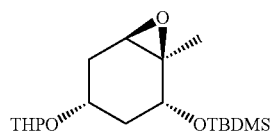

6

After that, the above-mentioned compound 6 is dissolved in a solvent such as toluene and a reaction is carried out by addition of aluminum isopropoxide so that a 7-oxabicyclo [4.1.0] ring is opened to form hydroxyl group and exo-methylene group at 1-position and 2-position, respectively, whereupon (1R-(1β,3α,5α))-3-[(tert-butyldimethylsilyl)oxy]-2-methylene-5-(tetrahydro-2-pyranyloxy)cyclohexanol (compound 7) is produced. Here, it is also possible to use aluminum alkoxide such as aluminum tert-butoxide instead of aluminum isopropoxide. Said compound is a kind of the compound represented by the formula (I). Its chemical formula is shown below.

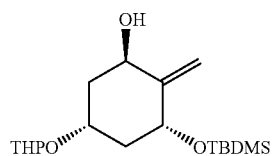

7

The above-mentioned compound 7 is further dissolved in a solvent such as DMF, a base such as imidazole is added thereto and a reaction is carried out under cooling with ice by addition of a silylating agent such as tert-butyldimethylchlorosilane so that hydroxyl group at 1-position is protected as tert-butyldimethylsilyloxy group to produce (3R,5R)-3,5-bis [(tert-butyldimethylsilyl)oxy]-2-methylene-1-(tetrahydro-2-pyranyloxy)cyclohexane (compound 8). Said compound is a kind of the compound represented by the formula (I). Its chemical formula is shown below.

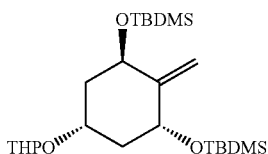

8

After that, the above-mentioned compound 8 is dissolved in a solvent such as methanol, an acid catalyst such as pyridinium p-toluenesulfonate (PPTS) is added thereto and a reaction is carried out, for example, on a water bath of 50 to 55° C. so that tetrahydro-2-pyranyloxy group at 1-position is deprotected to convert to hydroxyl group whereupon (3R,5R)-3,5-bis[(tert-butyldimethylsilyl)oxy]-4-methylenecyclohexanol (compound 9) is produced. Said compound is a kind of the compound represented by the formula (I). Its chemical formula is shown below.

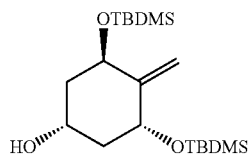

9

Synthetic example for the vitamin D derivative which is the final product from the above-mentioned compound 9 may follow a known method. Examples of the known method are those which are disclosed, for example, in the reaction step formulae I and II in Japanese Patent Laid-Open No. 05/186,421 and in the scheme II in Japanese Patent Laid-Open No. 2001/504,135.

Production of 1α-hydroxy-2-methylene-19-nor-17-isopropylcalciferol (compound 15, 2-MP) from (3R,5R)-3,5-bis[(tert-butyldimethylsilyl)oxy]-4-methylenecyclohexanol (compound 9) is able to be carried out a known common process.

For example, a solution of (3R,5R)-3,5-bis[(tert-butyldimethylsilyl)oxy]-4-methylenecyclohexanol (compound 9) in toluene is made to react with aluminum isopropoxide and cyclohexanone to produce (3R,5R)-3,5-bis[(tert-butyldimethylsilyl)oxy]-4-methylenecyclohexanone (compound 10).

After that, n-BuLi (n-butyl lithium) is added in an argon stream at −78° C. with stirring to a solution of diisopropylamine in anhydrous THF and methyl (trimethylsilyl) acetate is added thereto followed by subjecting to a reaction with the above-mentioned carbonyl compound (compound 10) to produce methyl [(3'R,5'R)-3',5'-bis[(tert-butyldimethylsilyl)oxy]-4'-methylenecyclohexylidene]acetate (compound 11).

Then diisobutyl aluminum hydride is added to a stirring solution of the above-mentioned methyl ester (compound 11) in toluene/methylene chloride at −78° C. in an argon stream and the mixture is stirred at −78° C. for 1 hour and at −46° C. for 25 minutes to produce 2-[(3'R, 5'R)-3',5'-bis [(tert-butyldimethylsilyl)-oxy]-4'-methylenecyclohexylidene]ethanol (compound 12).

After that, n-BuLi (n-butyl lithium) is added to the above-mentioned allyl alcohol compound (compound 12)/anhydrous THF in an argon stream at 0° C. and then tosyl chloride/anhydrous THF is added thereto. To the reaction solution is added a mixture prepared by addition of n-BuLi to diphenyl phosphine/anhydrous THF in an argon stream at 0° C. to complete the reaction. The solvent is evaporated, the residue is dissolved in methylene chloride and hydrogen peroxide is added thereto at 0° C. to produce {2-[(3'R,5'R)-3',5'-bis[(tert-butyldimethylsilyl)oxy]-4'-methylenecyclohexylidene]ethyl}-diphenylphosphine oxide (compound 13).

Then, n-BuLi is added to a solution of the above-mentioned phosphine oxide compound (compound 13)/anhydrous THF in an argon stream with stirring and the mixture is cooled at −78° C. and subjected to a Witting-Horner coupling with Grudmann ketone which is previously preserved at −78° C. to produce a vitamin D (compound 14) where hydroxyl groups at 1- and 3-positions are protected with tert-butyldimethylsilyl group.

With regard to the Grudmann ketone, a compound represented by the following formula (IV) is available. When the group R at 1-position of this compound is modified, various kinds of vitamin D derivatives are able to be produced.

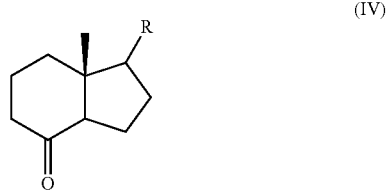

(IV)

(In the formula, R is any of representative side chains which are known for compounds of a vitamin D type. To be more specific, R is a linear, branched or cyclic and saturated or unsaturated hydrocarbon radical having 1 to 35 carbon atom(s) and may be a hydrocarbon radical which may contain one or more additional substituent (s) such as hydroxyl group, protected hydroxyl group, fluoro group, carbonyl group, ester group, epoxy group, amino group or other hetero atom group. Preferred side chain of this type is represented by the following structure.

[In the formula, stereochemical center (corresponding to C-20 in a steroid number) may be in R or S configuration (that is, either a natural configuration around carbon 20 or a 20-epi configuration); Z is selected from Y, —OY, —CH$_2$OY, —C≡CY and —CH═CHY wherein a double bond may have cis or trans-geometry; Y is selected from hydrogen atom, methyl group, —COR$^7$ and the following radical structure

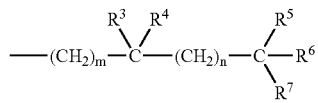

in which m and n each independently is an integer of 0 to 5; R$^3$ is selected from hydrogen atom, heavy hydrogen atom, hydroxyl group, protected hydroxyl group, fluoro group, trifluoromethyl group and a C$_{1-5}$ alkyl group which may be linear or branched and may have hydroxyl or protected hydroxyl group; R$^4$, R$^5$ and R$^6$ each independently is selected from heavy hydrogen atom, a deuteroalkyl group, hydrogen atom, fluoro group, trifluoromethyl group and a C$_{1-5}$ alkyl group which may be linear or branched and may have hydroxyl or protected hydroxyl group; R$^3$ and R$^4$ may be bonded together to form oxo group, an alkylidene group, ═CR$^4$R$^5$ group or —(CH$_2$)$_p$— group (in the formula, p is an integer of 2 to 5); R$^5$ and R$^6$ may be bonded together to form oxo group or —(CH$_2$)$_q$— group (in the formula, q is an integer of 2 to 5); R$^7$ is hydrogen atom, hydroxyl group, protected hydroxyl group or a $C_{1-5}$ alkyl group where any of —CH groups at 20, 22 or 23-positions in the side chain may be substituted with nitrogen atom; and any of —CH(CH$_3$)—, —CH(R$^5$)— and —CH(R$^4$)— at 20, 22 and 23-positions may be substituted with oxygen or sulfur atom.]

A wavy line to methyl group of C-20 shows that the carbon 20 may have any of R and S configurations.)

Important specific examples of the side chain having a natural 20R configuration are the structures represented by the following formulae (a), (b), (c), (d) and (e) (i.e., the side chain which takes place in 25-hydroxy vitamin $D_3$ (a), vitamin $D_3$ (b), 25-hydroxyvitamin $D_2$ (c), vitamin $D_2$ (d) and a C-24 epimer of 25-hydroxyvitamin $D_2$ (e)).

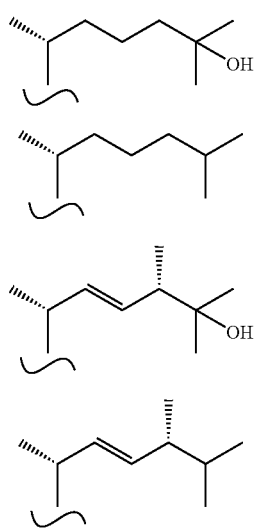

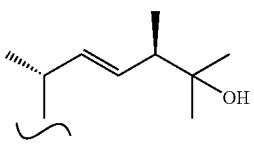

After that, a protective group is removed from the above-mentioned protected vitamin compound (compound 14) to give 1α-hydroxy-2-methylene-19-nor-17-isopropylcalciferol (compound 15; 2-MP).

In place of a process for producing the compounds 4 to 9 of the present invention from (R)-(−)-carvone via the above-mentioned compounds 2 and 3, it is also possible to produce the compound of the present invention in a similar manner from (S)-(+)-carvone. It is further possible to produce compounds having other substituent by conversion of methylene group at 4-position of (3R,5R)-3,5-bis[(tert-butyldimethylsilyl)oxy]-4-methylene-1-(tetrahydro-2-pyranyloxy)cyclohexane (compound 8) to a carbonyl group (compound 16). For example, it is possible to induce various compounds by converting the above-mentioned carbonyl group to an alkyl group (2) via an alkylidene group (1), to amino group (4) via imino group, oxime (3) or to hydroxyl group (5) from said carbonyl group (refer to chem. 17). In the formulae, each of $R^8$, $R^9$, $R^{10}$, $R^{11}$ and $R^{12}$ may be any of hydrogen atom, heavy hydrogen atom, fluorine atom, hydroxyl group, protected hydroxyl group, an alkyl group, an aryl group, an alkoxy group, a hydroxyalkoxy group, a fluoroalkoxy group, an arylalkoxy group, an aryloxy group, etc.

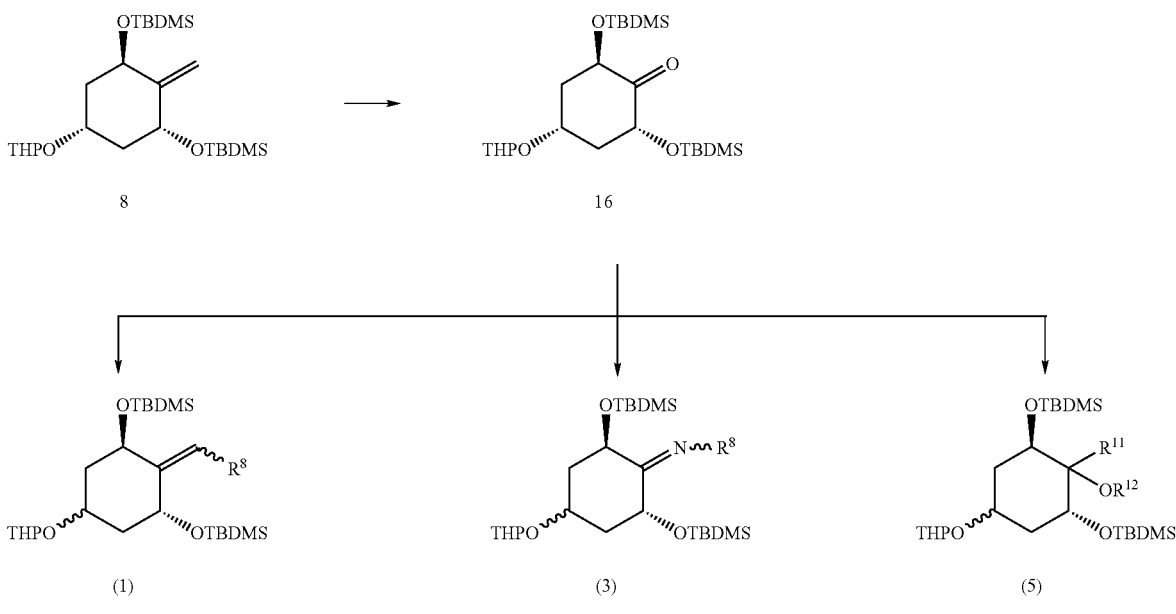

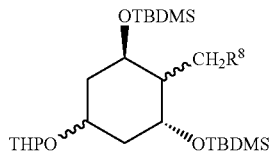

(2)

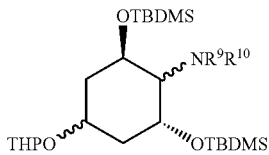

(4)

It is further possible to produce 19-nor-vitamin D derivatives having various substituents such as methylene group or ethylidene group at 2-position from those compounds (the above-mentioned compounds (1) to (5)) according to a known method (such as a method disclosed in reaction step formulae I and II in Japanese Patent Laid-Open No. 05/186,421 and in scheme II in Japanese Patent Laid-Open No. 2001/504,135).

EXAMPLES

The present invention will now be illustrated in detail by way of Referential Examples and Examples although the present invention is not limited by those Referential Examples and Examples.

Referential Example 1

Preparation of (1R-(1α,4α,6α)-1-methyl-4-(1-methylethenyl)-7-oxabicyclo[4.1.0]heptan-2-one (compound 2)

(R)-(−)-Carvone (compound 1) (60 g, 0.40 mol) was dissolved in 390 ml of methanol, 30% hydrogen peroxide solution (133 g, 1.17 mol) was added thereto, 6M NaOH (32.7 g) was dropped thereinto under cooling with ice and the mixture was stirred at the same temperature for 3 hours. Water (1,170 ml) was added to the reaction solution, the mixture was extracted with tert-butyl methyl ether (500 ml) twice, the extract was washed with water and brine, dried over $Na_2SO_4$ and the solvent was evaporated in vacuo to give the title compound (compound 2) (62.5 g, yield 98%) as a colorless oily product. Its NMR data is shown below.

$^1$H-NMR (CDCl$_3$) 4.77 (1H, brs), 4.70 (1H, brs), 3.43 (1H, dd, J=1.1, J=3.1), 2.70 (1H, m), 2.57 (1H, dd, J=6.1, J=17.6), 2.36 (1H, m), 2.01 (1H, dd, J=11.6, J=17.6), 1.89 (1H, m), 1.70 (3H, s), 1.40 (3H, s)

Referential Example 2

Preparation of (1S-(1α,2α,4α,6α))-1-methyl-4-(1-methylethenyl)-7-oxabicyclo-[4.1.0]heptan-2-ol (compound 3)

The above-mentioned compound 2 (50.0 g, 0.30 mol) was dissolved in methanol (750 ml), cesium (III) chloride heptahydrate (56.0 g, 0.15 mol) was added thereto, sodium borohydride (11.4 g, 0.30 mol) was gradually added thereto under cooling with ice and the mixture was stirred at the same temperature for 1 hour. Water (650 ml) was added thereto, the mixture was extracted with methylene chloride (1,200 ml, 650 ml and 650 ml), the extract was washed with water and dried over $Na_2SO_4$ and the solvent was evaporated in vacuo to give the title compound (compound 3) (49.9 g, yield 99%) as a colorless oily product. Its NMR data is shown below.

$^1$H-NMR (CDCl$_3$) 4.71 (2H, m), 3.89 (1H, m), 3.13 (1H, m), 2.15 (2H, m), 1.96 (1H, m), 1.71 (3H, s), 1.66 (1H, m), 1.39 (3H, s), 1.19 (1H, m)

Example 1

Preparation of (1R-(1α,2α,4α,6α)-2-[(tert-butyldimethylsilyl)oxy]-1-methyl-4-(1-methylethenyl)-7-oxabicyclo[4.1.0]heptane (compound 4)

The above-mentioned compound 3 (49.5 g, 0.294 mol) was dissolved in DMF (500 ml), imidazole (24.0 g, 0.353 mol) was added thereto, tert-butyldimethylchlorosilane (53.2 g, 0.353 mol) was added thereto under cooling with ice and the mixture was stirred at room temperature for 15 hours. Water (1,500 ml) was added to the reaction product, the mixture was extracted with ethyl acetate (1,500 ml), the extract was washed with water and dried over $Na_2SO_4$ and the solvent was evaporated in vacuo to give the title compound (compound 4) (84 g, quantitatively) as a colorless oily product. Its NMR data is shown below.

$^1$H-NMR (CDCl$_3$) 4.69 (2H, m), 3.84 (1H, dd, J=6.3, J=10.3), 3.10 (1H, s), 2.11 (2H, m), 1.80 (1H, m), 1.69 (3H, s), 1.63 (1H, m), 1.32 (3H, s), 1.16 (1H, m), 0.91 (9H, s), 0.10 (3H, s), 0.07 (3H, s)

Example 2

Preparation of (1R-(1α,2α,4α,6α))-2-[(tert-butyldimethylsilyl)oxy]-1-methyl-7-oxabicyclo[4.1.0]heptan-4-ol (compound 5)

The above-mentioned compound 4 (65 g, 0.23 mol) was dissolved in methanol (260 ml) and methylene chloride (1,300 ml) and ozone gas was introduced thereinto at −65° C. until the color of the reaction solution became blue. Nitrogen gas was introduced thereinto to remove excessive ozone, then triethylamine (140 g, 1.38 mol), N,N-dimethyl-4-aminopyridine (3.3 g, 0.023 mol) and acetic anhydride (117 g, 1.15 mol) were successively added thereto and the mixture was raised up to room temperature and stirred at 40° C. for 9 hours. After cooling, the reaction product was poured into ice water (1,500 ml), the organic layer was washed with water and dried over $Na_2SO_4$, the solvent was evaporated in vacuo and the residue was subjected to a silica gel chromatography (n-hexane/ethyl acetate=5:1) to give the title compound (compound 5) (35 g, yield 57%) as a colorless oily product. Its NMR data is shown below.

$^1$H-NMR (CDCl$_3$) 4.16 (1H, t, J=3.4), 4.05 (1H, d, J=8.2), 3.82 (1H, m), 3.05 (1H, d, J=4.2), 2.11 (2H, m), 1.78 (2H, m), 1.37 (3H, s), 0.91 (9H, s), 0.15 (3H, s), 0.13 (3H, s)

Example 3

Synthesis of (1R-(1α,2α,4α,6α))-2-[(tert-butyldimethylsilyl)oxy]-1-methyl-4-(tetrahydro-2-pyranyloxy)-7-oxabicyclo[4.1.0]heptane (compound 6)

The above-mentioned compound 5 (24.0 g, 0.093 mol) was dissolved in methylene chloride (200 ml), then p-toluenesulfonic acid (10 mg) and 3,4-dihydro-2H-pyran (8.6 g, 0.102 mol) were added thereto and the mixture was stirred at room temperature for 20 hours. The reaction product was washed with a saturated aqueous solution of sodium bicarbonate and a brine and dried over $Na_2SO_4$ and the solvent was evaporated in vacuo. The residue was subjected to a silica gel column chromatography (n-hexane/ethyl acetate=9:1) to give the title compound (compound 6) (25.3 g, yield 79%) as a colorless oily product. Its NMR data is shown below.

$^1$H-NMR (CDCl$_3$) 4.62 (1H, m), 3.88 (2H, m), 3.74 (1H, m), 3.47 (1H, m), 3.10 (1H, t, J=1.3), 2.48 (1H, m), 2.10 (1H, m), 1.82-1.23 (8H, m), 1.30 (3H, s), 0.90 (9H, s), 0.09 (3H, s), 0.07 (3H, s)

Example 4

Preparation of (1R-(1β,3α,5α))-3-[(tert-butyldimethylsilyl)oxy]-2-methylene-5-(tetrahydro-2-pyranyloxy)cyclohexanol (Compound 7)

The above-mentioned compound 6 (25.0 g, 0.073 mol) was dissolved in toluene (300 ml), aluminum isopropoxide (29.8 g, 0.146 mol) was added thereto and the mixture was heated to reflux for 19 hours. After cooling, the reaction product was poured into cold 1M HCl (150 ml), an organic layer was washed with a saturated aqueous solution of sodium bicarbonate and a brine and dried over $Na_2SO_4$ and the solvent was evaporated in vacuo to give the title compound (compound 7) (25.0 g, quantitatively) Its NMR data is shown below.

$^1$H-NMR (CDCl$_3$) 5.13 (1H, m), 4.97 (1H, brs), 4.71 (1H, m), 4.50 (2H, m), 4.20 (1H, m), 3.90 (1H, m), 3.50 (1H, m), 2.31 (2H, m), 1.84-1.23 (8H, m), 0.91 (9H, s), 0.08 (3H, s), 0.07 (3H, s)

Example 5

Preparation of (3R,5R)-3,5-bis[(tert-butyldimethylsilyl)oxy]-4-methylene-1-(tetrahydro-2-pyranyloxy)cyclohexane (compound 8)

The above-mentioned compound 7 (25.0 g, 0.073 mol) was dissolved in DMF (150 ml), imidazole (10.9 g, 0.16 mol) was added thereto, then tert-butyldimethylchlorosilane (12.1 g, 0.08 mol) was added thereto under cooling with ice and the mixture was stirred at room temperature for 15 hours. Diisopropyl ether (300 ml) was added thereto, the mixture was washed with water and a brine and dried over $Na_2SO_4$ and the solvent was evaporated in vacuo to give the title compound (compound 8) (34 g, quantitatively) as a colorless oily product. Its NMR data is shown below.

$^1$H-NMR (CDCl$_3$) 5.02 (1H, m), 4.83 (1H, s), 4.74 (1H, m), 4.45 (2H, m), 4.18 (1H, m), 3.90 (1H, m), 3.49 (1H, m), 2.30 (1H, m), 2.10 (1H, m), 1.83-1.25 (8H, m), 0.91 (9H, s), 0.86 (9H, s), 0.068 (3H, s) 0.062 (3H, s), 0.010 (3H, s), 0.005 (3H, s)

Example 6

Preparation of (3R,5R)-3,5-bis[(tert-butyldimethylsilyl)oxy]-4-methylenecyclohexanol (Compound 9)

The above-mentioned compound 8 (15.9 g, 34.8 mol) was dissolved in methanol (150 ml), pyridinium p-toluenesulfonate (75 mg) was added thereto and the mixture was stirred at 50 to 55° C. on a water bath for 1 hour. After cooling, potassium carbonate (50 mg) was added thereto, the solvent of the reaction solution was evaporated in vacuo and the residue was subjected to a silica gel chromatography (n-hexane/ethyl acetate=from 20:1 to 10:1) to give the title compound (compound 9) (7.0 g, yield 54%) as a colorless oily product. Its NMR data is shown below.

$^1$H-NMR (CDCl$_3$) 5.04 (1H, t, J=1.83), 4.92 (1H, s), 4.73 (1H, dd, J=4.58, J=9.52), 4.59 (1H, t, J=4.0), 4.14 (1H, m), 3.55 (1H, brs), 2.11 (1H, m), 1.95 (1H, m), 1.79 (1H, m), 1.63 (1H, m), 0.91 (9H, s), 0.89 (9H, S), 0.098 (3H, s), 0.086 (3H, s), 0.070 (3H, s), 0.063 (3H, s)

ADVANTAGES OF THE INVENTION

Due to the above-mentioned constitution, the present invention is able to provide a novel synthetic intermediate for the total synthesis of vitamin D derivatives or, particularly, an intermediate for the synthesis of a 19-nor-vitamin D derivative in which an exo-methylene group constituting the double bond outside the A ring of the vitamin D derivative is substituted with two hydrogen atoms. The intermediate as such is able to be produced from carvone which is a less expensive material.

The invention claimed is:

1. A compound represented by the following formula (I):

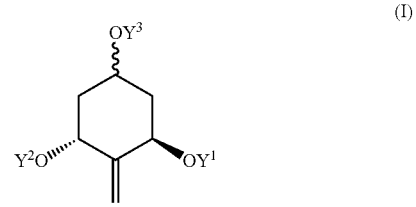

(I)

wherein $Y^1$ and $Y^2$ may be same or different and each is a protective group for hydroxyl group;

and $Y^3$ is hydrogen atom where a group $Y^3O$— may be either in R configuration or S configuration.

2. The compound according to claim 1 where said $Y^1$ and $Y^2$ are tert-butyldimethylsilyl group, and said $Y^3$ is hydrogen atom.

3. A compound represented by the following formula (I):

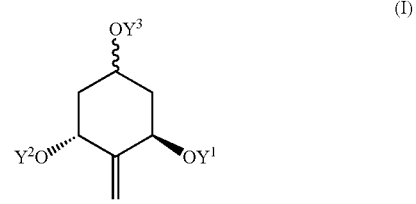

(I)

wherein $Y^1$ and $Y^2$ may be same or different and each is a protective group for hydroxyl group;

and Y³ is a protective group for hydroxyl group where a group Y³O— may be either in R configuration or S configuration.

4. A compound represented by the following formula (I):

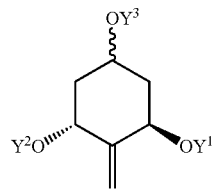

(I)

wherein Y¹ is hydrogen atom and Y² is a protective group for hydroxyl group; and Y³ is a protective group for hydroxyl group where a group Y³O— may be either in R configuration or S configuration.

5. The compound according to claim 3 where said Y¹ and Y² are tert-butyldimethylsilyl group, and said Y³ is any one of tetrahydro-2-pyranyl group, acetyl group, methoxymethyl group and benzoyl group.

6. The compound according to claim 4 where said Y¹ is hydrogen atom, said Y² is tert-butyldimethylsilyl group, and said Y³ is any one of tetrahydro-2-pyranyl group, acetyl group, methoxymethyl group and benzoyl group where said Y³O— is in an R configuration.

\* \* \* \* \*